(12) United States Patent
Bellet et al.

(10) Patent No.: US 12,216,031 B2
(45) Date of Patent: Feb. 4, 2025

(54) STATION AND METHOD FOR MEASURING AIRBORNE MOLECULAR CONTAMINATION

(71) Applicant: PFEIFFER VACUUM, Annecy (FR)

(72) Inventors: Bertrand Bellet, Annecy (FR); Julien Bounouar, Annecy (FR); Olivier Le Barillec, Annecy (FR)

(73) Assignee: PFEIFFER VACUUM, Annecy (FR)

( * ) Notice: Subject to any disclaimer, the term of this patent is extended or adjusted under 35 U.S.C. 154(b) by 313 days.

(21) Appl. No.: 17/907,473

(22) PCT Filed: Mar. 26, 2021

(86) PCT No.: PCT/EP2021/058023
§ 371 (c)(1),
(2) Date: Sep. 27, 2022

(87) PCT Pub. No.: WO2021/198107
PCT Pub. Date: Oct. 7, 2021

(65) Prior Publication Data
US 2023/0221220 A1    Jul. 13, 2023

(30) Foreign Application Priority Data
Apr. 1, 2020 (FR) ................................ 2003266

(51) Int. Cl.
*G01N 1/26*    (2006.01)
*G01N 1/22*    (2006.01)
(Continued)

(52) U.S. Cl.
CPC .............. *G01N 1/26* (2013.01); *G01N 1/2273* (2013.01); *G01N 33/0011* (2013.01); *G01N 2001/244* (2013.01)

(58) Field of Classification Search
CPC .... G01N 1/26; G01N 1/2273; G01N 33/0011; G01N 35/1095; G01N 2001/244
See application file for complete search history.

(56) References Cited

U.S. PATENT DOCUMENTS

| 5,246,668 A * | 9/1993 | MacCallum ....... G01N 33/0031 422/62 |
| 5,553,507 A | 9/1996 | Basch et al. |

(Continued)

FOREIGN PATENT DOCUMENTS

| CA | 2274736 A1 * | 12/1999 | ............... G01N 1/26 |
| EP | 0 664 449 A1 | 7/1995 | |

(Continued)

OTHER PUBLICATIONS

International Search Report and Written Opinion issued Jun. 2, 2021, in PCT/EP2021/058023 filed Mar. 26, 2021, 11 pages.

*Primary Examiner* — John Fitzgerald
(74) *Attorney, Agent, or Firm* — Oblon, McClelland, Maier & Neustadt, L.L.P.

(57) ABSTRACT

A measurement station for measuring airborne molecular contamination includes at least one gas analyser, at least two controllable isolation valves connected in parallel to the input of the at least one gas analyser, a conditioning pump, at least two calibrated orifices connected in parallel to the input of the conditioning pump, at least one distributor to connect each controllable isolation valve with, on one side, a sampling line and, on the other side, a calibrated orifice, and a control unit linked to the controllable isolation valves. The control unit commands the opening or the closing of the controllable isolation valves in order to be able to connect the at least one gas analyser with at least one sampling line.

15 Claims, 2 Drawing Sheets

(51) Int. Cl.
*G01N 33/00* (2006.01)
*G01N 1/24* (2006.01)

(56) References Cited

U.S. PATENT DOCUMENTS

| | | | | |
|---|---|---|---|---|
| 7,028,563 | B2 * | 4/2006 | Gamache | F17D 3/10 |
| | | | | 73/863.33 |
| 7,096,750 | B2 * | 8/2006 | Kreck | G01N 1/26 |
| | | | | 73/863.33 |
| 11,768,134 | B2 * | 9/2023 | Bounouar | G01N 33/0011 |
| | | | | 73/23.2 |
| 11,953,484 | B2 * | 4/2024 | Bounouar | G05D 7/0658 |
| 12,066,355 | B2 * | 8/2024 | Coulomb | G01M 3/20 |
| 2005/0217391 | A1 | 10/2005 | Gamache et al. | |
| 2006/0108221 | A1 * | 5/2006 | Goodwin | G01N 33/0009 |
| | | | | 204/424 |
| 2013/0259711 | A1 * | 10/2013 | Burggraf | F04D 19/042 |
| | | | | 417/199.1 |

FOREIGN PATENT DOCUMENTS

| | | | |
|---|---|---|---|
| FR | 3 081 558 A1 | 11/2019 | |
| WO | WO-2024061629 A1 * | 3/2024 | G01N 1/2273 |

\* cited by examiner

STATION AND METHOD FOR MEASURING AIRBORNE MOLECULAR CONTAMINATION

The present invention relates to a measurement station for measuring airborne molecular contamination, intended in particular for monitoring molecular contamination concentrations in the atmosphere of cleanrooms, such as the cleanrooms of semiconductor manufacturing plants. The present invention relates also to a method for measuring airborne molecular contamination by means of such a station.

In the semiconductor fabrication industry, the substrates, such as the semiconductor wafers or the photomasks, have to be protected from airborne molecular contamination (or AMC) in order to prevent it from damaging the chips or electronic circuits of the substrates. For that, the substrates are contained in atmospheric transportation and storage boxes, allowing the substrates to be transported from one piece of equipment to the next or them to be stored between two fabrication steps. Moreover, the transportation boxes and the pieces of equipment are arranged inside cleanrooms in which the particle level is minimized and the temperature, relative humidity and pressure are maintained at precise levels.

In cleanrooms, the airborne gaseous species can have different sources and different natures, including for example acids, bases, condensable elements, doping elements. These molecules can originate from the air inside the semiconductor fabrication plant or can be given off notably by the semiconductor wafers that have undergone prior fabrication operations.

Gas analysers present in the cleanrooms make it possible to assess the concentration of the airborne gaseous species in real time, notably that of moisture and of some acids. The measured concentrations are sometimes very low, such as on the ppm or ppb scale. These gas analysers measure the gaseous atmosphere of the surroundings, so it is therefore necessary to provide a gas analyser in each zone to be tested of the cleanroom.

There is a need to increase the number of gaseous species measured and the number of test zones in order to reduce the risks of contamination of the substrates. However, multiplying the number of analysers per zone and multiplying these zones to be tested rapidly makes this solution very costly.

To reduce the costs, a measurement unit is proposed that combines different analysers. The unit is provided with a number of input ports each addressing a particular test zone of the cleanroom. The cleanrooms can be of significant dimensions and, with the number of test zones also increasing, it proves necessary to use a significant number of sampling lines, the lengths of these lines usually reaching several tens of metres. This lengthy path for the gas to reach the measurement cell of the analyser takes time, which means a delay in the information. It is in fact necessary to "replace" all the volume contained in the sampling line with the gas to be measured at least once, this gas also potentially easily sticking to the walls of the line by adsorption, in particular for the so-called polar gaseous species to be measured. It can then be difficult to obtain a measurement that is truly representative of the concentration of the gaseous species in the test zone without waiting for a very long time on each change of test zone.

One solution consists in simultaneously sucking into all the sampling lines. The gas is thus constantly sucked into all the sampling lines by means of a common discharge. However, since the sampling lines can be very long, they can adsorb then subsequently release a part of the gaseous species conveyed. The measurement is then partly the reflection of a preceding measurement, which can complicate the interpretation to be given to the results and the decisions to be taken if thresholds are exceeded.

The document WO2019/228844 describes a measurement station in which a sampling solenoid valve is arranged on each sampling line, two conditioning solenoid valves are arranged bypassing the input of a conditioning pump and two measurement solenoid valves are arranged bypassing the input of a gas analyser. This configuration makes it possible to connect at least one sampling line, for which the measurement is programmed following a sampling line currently being measured by the gas analyser, with the conditioning pump. A maximum pumping throughput can thus be used for the conditioning which can be performed in parallel.

A degassing of the line just before it is measured can however prove inadequate to totally eliminate the memory effect of the line in certain applications, notably when the gaseous species to be monitored tend to adhere particularly to the walls, as is the case for certain acids like HF, or such as ammonia $NH_3$.

One of the aims of the present invention is to propose a measurement station and method which at least partially resolve one of the abovementioned drawbacks.

To this end, the subject of the invention is a measurement station for measuring airborne molecular contamination comprising:
 at least one gas analyser,
 at least two controllable isolation valves connected in parallel to the input of the at least one gas analyser,
 a conditioning pump,
 characterized in that the measurement station also comprises:
 at least two calibrated orifices connected in parallel to the input of the conditioning pump,
 at least one distributor configured to connect each controllable isolation valve with, on one side, a sampling line and, on the other side, a calibrated orifice, and
 a control unit linked to the controllable isolation valves and configured to command the opening or the closing of the controllable isolation valves in order to be able to connect the at least one gas analyser with at least one sampling line.

In operation, the conditioning pump continually pumps in all the sampling lines simultaneously, through the calibrated orifices, including the sampling line in which a measurement is performed. All the sampling lines can thus be subjected to a continuous pumping, which, on the one hand, ensures effective conditioning and, on the other hand, ensures that the lines are always ready for a measurement, which makes it possible to optimize the rate of the measurement station.

The calibrated orifices are simple mechanical pieces, they are inexpensive compared to valves. In addition, they do not require preliminary adjustments or settings, or particular maintenance, which makes it possible to limit the labour costs and the installation time.

The measurement station is therefore simple to implement and there are no risks of drifts of the settings in time. It is also possible to change a sampling line, notably its length, without needing to perform new settings, and without that being detrimental to the measurements in the other sampling lines.

The measurement station can, furthermore, comprise one or more of the features which are described hereinbelow, taken alone or in combination.

The measurement station is, for example, configured to guarantee a flow of the gases at critical regime in the narrowest section of the calibrated orifices. The critical regime is reached when the pressure downstream of the calibrated orifice is such that the ratio of the downstream pressure to the upstream pressure is less than or equal to a critical value, the speed of the gas (at the downstream pressure) in the narrowest section of the calibrated orifice being then equal to the speed of sound. This critical value is 0.53 in air, assuming that most of the gas circulating in the sampling lines is air.

The throughput through the calibrated orifices is then sonic, which makes the backscattering of gas through the calibrated orifices virtually impossible, and therefore makes interferences between the different sampling lines impossible. Although there is no mechanical barrier (there are no valves) between the sampling lines, the flow dimensions of the calibrated orifices allowing the flow at critical regime in the calibrated orifices thus form a "fluidic barrier" preventing cross-contamination between the sampling lines and allowing for a pumping that is evenly distributed in all the sampling lines.

The at least two calibrated orifices can define a gas stream at critical regime of less than 1.69 Pa·m$^3$/s (1 slm).

The at least two calibrated orifices can have a dimension less than 6/10 mm, such as less than 4/10 mm.

The throughput of the conditioning pump is, for example, greater than 25.35 Pa·m$^3$/s (15 slm).

The measurement station can comprise a number of sampling lines greater than two, such as greater than or equal to 16, such as greater than or equal to 128.

The distributor can comprise a collector having a common section connected to the conditioning pump, at least two main branches connected to the common section, at least two secondary branches connected to the main branches, the secondary branches bearing a respective calibrated orifice, the calibrated orifices being connected to the controllable isolation valves and to the sampling lines.

The measurement station can comprise a pressure sensor interposed between the conditioning pump and the at least two calibrated orifices. The control unit can be configured to generate a warning when the pressure measured by the pressure sensor is greater than 50 000 Pa (500 mbar), even 40 000 (400 mbar). The pressure sensor makes it possible to check that the pressure condition downstream of the calibrated orifices is indeed fulfilled to guarantee the flow at critical regime through the calibrated orifices.

The sampling lines and the controllable isolation valves can have internal surfaces in contact with the gases, produced in materials limiting the adhesion of the gaseous species, such as one or more fluoropolymer materials.

Also a subject of the invention is a measurement method in a measurement station as described previously, characterized in that the at least one gas analyser is connected with one sampling line at a time, the conditioning pump continually pumping in all the sampling lines simultaneously.

DESCRIPTION OF THE DRAWINGS

Other advantages and features will emerge on reading the following description of a particular, but nonlimiting, embodiment of the invention, and the attached drawings in which.

In these figures, the elements that are identical bear the same reference numbers.

The following embodiments are examples. Although the description refers to one or more embodiments, that does not necessarily mean that each reference relates to the same embodiment, or that the features apply only to a single embodiment. Simple features of different embodiments can also be combined or swapped to provide other embodiments.

"Upstream" is understood to mean an element which is placed before another with respect to the direction of circulation of the gas to be pumped. By contrast, "downstream" is understood to mean an element placed after another with respect to the direction of circulation of the gas to be pumped.

Figure 1:
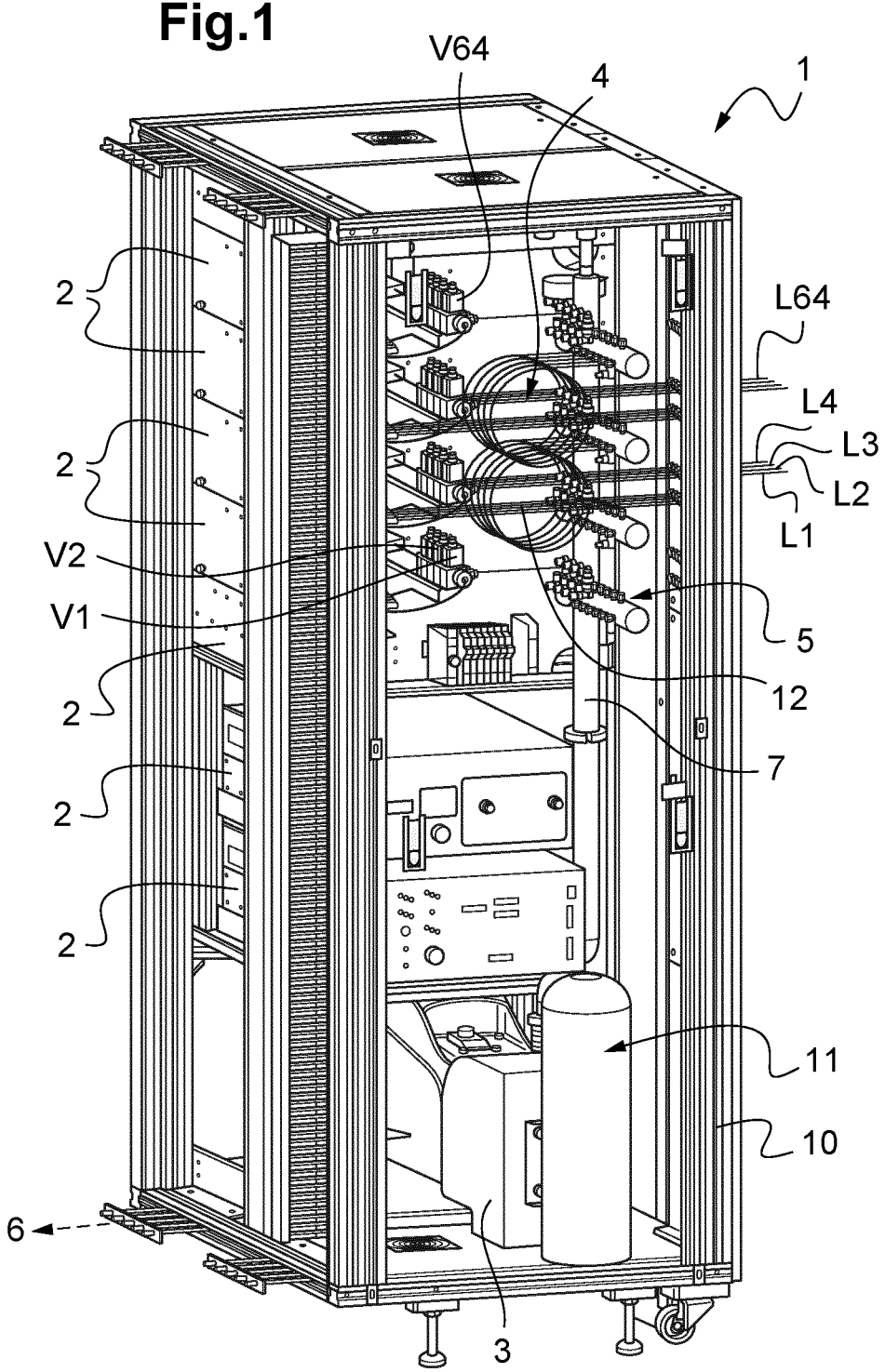
FIG. 1 represents a schematic view of elements of a station for measuring airborne molecular contamination, seen from the rear.

FIG. 1 shows an exemplary measurement station 1 for measuring airborne molecular contamination, intended in particular to monitor molecular contamination concentrations in the atmosphere of cleanrooms, such as the cleanrooms of semiconductor fabrication plants.

Figure 2:
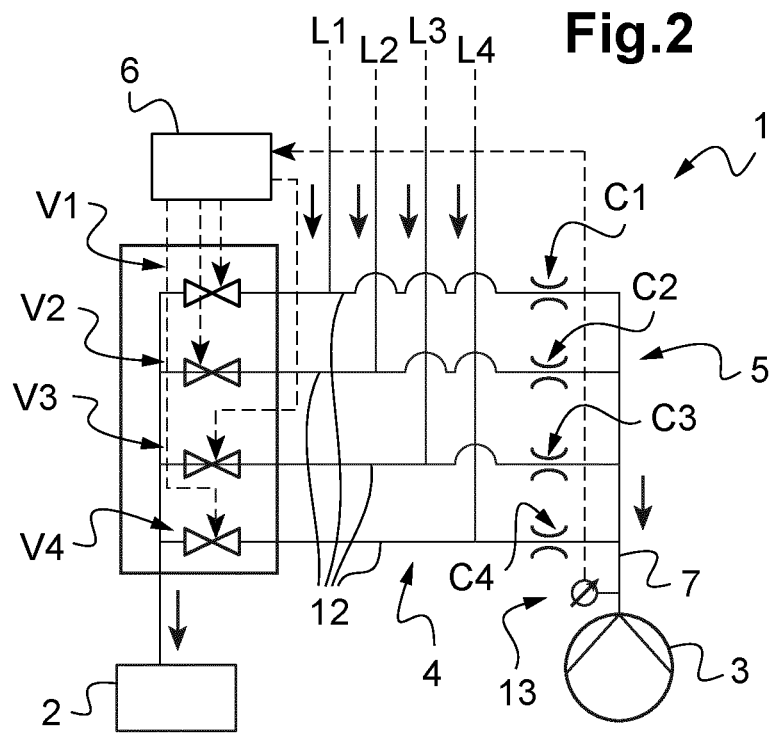
FIG. 2 represents a schematic view of elements of the measurement station of FIG. 1, in particular four sampling lines and one gas analyser.

As can be seen better in FIG. 2, the measurement station 1 comprises at least one gas analyser 2, at least two controllable isolation valves V1-V64 connected in parallel to the input of the at least one gas analyser 2, a conditioning pump 3, at least two calibrated orifices C1-C64 connected in parallel to the input of the conditioning pump 3 and at least one distributor 4 configured to connect each controllable isolation valve V1-V64 with, on one side, a sampling line L1-L64 and, on the other side, a calibrated orifice C1-C64.

The gas analyser 2 makes it possible to measure the concentration of at least one gaseous species in real time, that is to say with a measurement duration less than a few seconds, even a few minutes, with low concentrations lower than ppm or ppb. The gaseous species measured is, for example, an acid, such as hydrofluoric acid HF or hydrochloric acid HCl or a solvent, such as PGM EA (propylene glycol methyl ether). According to another example, the gaseous species is ammonia $NH_3$. The at least one gas analyser 2 also comprises an internal pump for taking gaseous samples. A gas analyser 2 can be adapted to measure a distinct gaseous species or a group of distinct gaseous species. There are seven gas analysers in the illustrative example of FIG. 1.

The end of each sampling line L1-L64 is intended to emerge in a test zone at ambient pressure, that is to say atmospheric pressure. The sampling lines L1-L4 link the measurement station 1 to distinct test zones, for example in a place distinct from a cleanroom. There are at least two sampling lines L1-L64 emerging in two distinct places. The measurement station 1 can comprise a number of sampling lines L1-L64 greater than or equal to 16, such as greater than or equal to 128. There are 64 sampling lines L1-L64 in the illustrative example of the measurement station 1 of FIG. 1. The length of the sampling lines L1-L4 can vary between the different test zones to be joined and can be a few metres or several tens of metres, such as more than 200 metres.

As can be seen in FIG. 2, the measurement station 1 also comprises a control unit 6 linked to the controllable isolation valves V1-V64 and configured to command the opening or the closing of the controllable isolation valves V1-V64 to be able to connect the at least one gas analyser 2 with at least one sampling line L1-L64. The controllable isolation valves V1-V64 are, for example, solenoid valves or pneumatic valves. They are controllable in on or off mode (open or closed) by the control unit 6.

The sampling lines L1-L64 and the controllable isolation valves V1-V64 can have internal surfaces in contact with the gases, produced in materials limiting the adhesion of the gaseous species, such as one or more fluoropolymer materials, such as perfluoroalkoxy (also called PFA) or polytetrafluoroethylene (also called PTFE).

The at least one gas analyser 2, the conditioning pump 3 and the at least one distributor 4 are, for example, mounted in a rack 10 of the measurement station 1, that can be connected to an electrical enclosure (not represented) supporting the control unit 6 for example. The rack 10 can also receive one or more gas cylinders 11 for the calibration of the at least one gas analyser 2.

Figure 3:
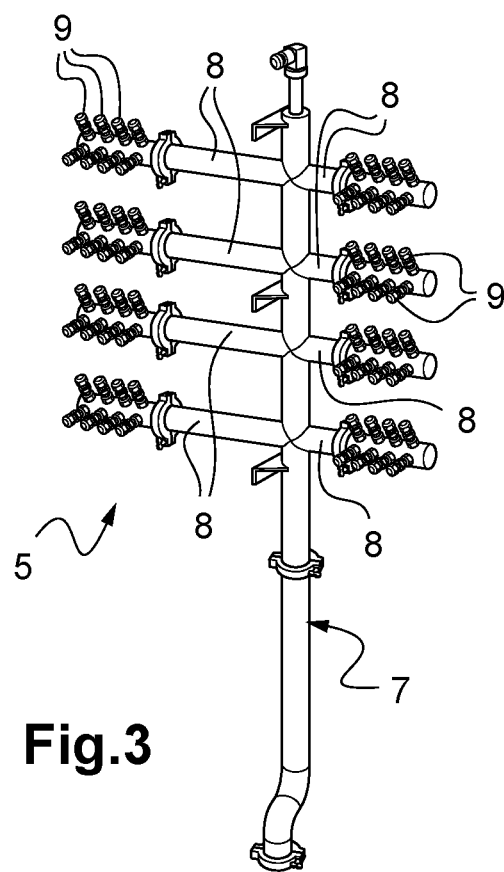
FIG. 3 shows an exemplary distributor of the measurement station of FIG. 1.

According to an exemplary embodiment that can be seen better in FIG. 3, the distributor 4 comprises a collector 5 having a common section 7, at least two main branches 8 connected to the common section 7, here eight of them, at least two secondary branches 9 connected to the main branches 8, here eight of them, the secondary branches 9 having a respective calibrated orifice C1-C64. The distributor 4 is, for example, of rigid structure, such as of stainless steel, each branch 8, 9 and the section 7 being formed by straight pipes, the cross section of the section 7 being greater than that of the main branches 8, which themselves have a cross section greater than that of the secondary branches 9. There is no need to provide special coatings limiting the adhesion of the gaseous species in the collector 4 because of the continual pumping by the conditioning pump 3.

The calibrated orifices C1-C64 are, for example, fixed to the secondary branches 9 by screwing or welding. The calibrated orifices C1-C64 are connected on the upstream side, in parallel to the sampling lines L1-L64 and to the valves V1-V64, by pneumatic "T" connectors 12.

The measurement station 1 can also comprise a pressure sensor 13 interposed between the conditioning pump 3 and the at least two calibrated orifices C1-C64, configured to measure the pressure downstream of the calibrated orifices C1-C64. This pressure sensor 13 is, for example, arranged on the common section 7 of the collector 5 (FIG. 2). The pressure sensor 13 makes it possible to check the correct operation of the measurement station 1, and notably that the downstream pressure is sufficiently low to allow a flow at critical regime through the calibrated orifices C1-C64.

In fact, the measurement station 1 can be configured for the flow of the gases to be at critical or "sonic" flow ("choked flow" in the literature) in the narrowest section of the calibrated orifice C1-C64. The critical regime is reached when the pressure downstream of the calibrated orifice C1-C64 is such that the ratio of the downstream pressure to the upstream pressure is less than or equal to a critical value, the speed of the gas (at the downstream pressure) in the narrowest section of the calibrated orifice being then equal to the speed of sound. This critical value is 0.53 in air, it being assumed that most of the gas circulating in the sampling lines is air.

The throughput through the calibrated orifices C1-C64 is then sonic, which makes the backscattering of gas through the calibrated orifices C1-C64 virtually impossible, and therefore makes interferences between the different sampling lines L1-L64 impossible. Although there is no mechanical barrier (there are no valves) between the sampling lines, L1-L64, the flow dimensions of the calibrated orifices C1-C64 allowing the flow at critical regime in the calibrated orifices C1-C64 thus form a "fluidic barrier" preventing cross-contamination between the sampling lines L1-L64 and allowing a pumping that is evenly distributed in all the sampling lines L1-L64.

The throughput through the calibrated orifices C1-C64 at critical regime is, for example, less than 1.69 Pa·m$^3$/s (1 slm), such as less than 1.352 Pa·m$^3$/s (0.8 slm). This flow is for example 1.1323 Pa·m$^3$/s (0.67 slm).

The at least two calibrated orifices C1-C64 have, for example, a dimension (the narrowest section) less than $6/10$ mm, such as less than $4/10$ mm. The calibrated orifices C1-C64 have, for example, a dimension equal to 0.28 mm.

The calibrated orifices C1-C64 of the measurement station 1 may or may not have the same cross section. They are for example pierced crystals (or other parts). The pumping capacity of the conditioning pump 3 is defined to be greater than the product of the throughput of the calibrated orifices C1-C64 by the number of calibrated orifices (or of sampling lines L1-L64). It is also chosen as a function of the desired rate of renewal in the sampling lines L1-L64. The throughput of the conditioning pump 3 is for example greater than 25.35 Pa·m$^3$/s (15 slm). The throughput of the conditioning pump 3 is greater than 64*0.67 slm in the illustrative example.

It is possible to monitor the pressure to ensure that it is sufficiently low at the conditioning pump 3 to guarantee the critical regime at the calibrated orifices C1-C64. For that, for example, the control unit 6 is configured to generate a warning when the pressure measured by the pressure sensor 13 exceeds 50 000 Pa (500 mbar), even 40 000 Pa.

These gas stream values at critical regime determined by the dimension of the narrowest section of the calibrated orifices C1-C64, from the pumping capacity of the conditioning pump 3 and from the number of sampling lines L1-L64 to be conditioned, make it possible to obtain a minimum acceptable rate of renewal in the sampling lines and to render the differences between the sampling lines L1-L64 negligible so that all the sampling lines L1-L64 can evenly distribute the pumping flow and no line is less well degassed than any other even if it is much shorter.

In operation, the gas analyser 2 is connected with one line at a time, the control unit 5 commanding a sequencing of the measurements by opening just one controllable isolation valve V1-V64 at a time and in turn.

The conditioning pump 3 pumps continually in all the sampling lines L1-L64 simultaneously, through the calibrated orifices C1-C64, including the sampling line L1-L64 in which a measurement is performed. All the sampling lines L1-L64 can thus be subjected to a continuous pumping, which ensures, on the one hand, effective conditioning and, on the other hand, that the lines are always ready for a measurement, which makes it possible to optimize the rate of the measurement station 1.

The calibrated orifices C1-C64 are simple mechanical parts, they are inexpensive compared to valves. Furthermore, they do not require preliminary adjustments or settings, or any particular maintenance, which makes it possible to limit the labour costs and the installation time.

The measurement station 1 is therefore simple to implement and there are no risks of drifts of the settings in time. It is also possible to change a sampling line, notably its length, without needing to carry out new settings, and without that being detrimental to the measurements in the other sampling lines L1-L64, given the impossibility of backscattering in the calibrated orifices C1-C64 at critical regime.

The invention claimed is:

1. A measurement station for measuring airborne molecular contamination comprising:
   at least one gas analyser,
   at least two controllable isolation valves connected in parallel to an input of the at least one gas analyser,
   a conditioning pump,
   at least two calibrated orifices connected in parallel to an input of the conditioning pump,
   at least one distributor configured to connect each controllable isolation valve with, on one side, a sampling line and, on the other side, a calibrated orifice, and
   a control unit linked to the controllable isolation valves and configured to command the opening or the closing of the controllable isolation valves in order to be able to connect the at least one gas analyser with at least one sampling line.

2. The measurement station according to claim 1, wherein the at least one sampling line includes a number of sampling lines greater than two.

3. The measurement station according to claim 1, wherein the distributor comprises a collector having a common section connected to the conditioning pump, at least two main branches connected to the common section, at least two secondary branches connected to the main branches, the secondary branches bearing a respective calibrated orifice, the calibrated orifices being connected to the controllable isolation valves and to the at least one sampling line.

4. The measurement station according to claim 1, further comprising a pressure sensor interposed between the conditioning pump and the at least two calibrated orifices, the control unit being configured to generate a warning when the pressure measured by the pressure sensor is greater than 50,000 Pa.

5. The measurement station according to claim 1, wherein the at least one sampling line and the controllable isolation valves have internal surfaces in contact with the gases, produced in materials that limit the adhesion of the gaseous species.

6. A measurement method in the measurement station according to claim 1, the method comprising:
   connecting the at least one gas analyser with one sampling line of the at least one sampling line at a time, and
   pumping continually via the conditioning pump in all the sampling lines of the at least one sampling line simultaneously.

7. The measurement station according to claim 1, wherein the at least one sampling line includes a number of sampling lines greater than 16.

8. The measurement station according to claim 1, wherein the at least one sampling line includes a number of sampling lines greater than or equal to 128.

9. The measurement station according to claim 1, wherein the at least one sampling line and the controllable isolation valves have internal surfaces in contact with the gases, produced in one or more fluoropolymer materials.

10. The measurement station according to claim 1, wherein the measurement station is configured to guarantee a flow of gases at critical regime in a narrowest section of the calibrated orifices.

11. The measurement station according to claim 10, wherein the measurement station is configured to guarantee a flow of the gases at critical regime for which a ratio of a downstream pressure to an upstream pressure is less than or equal to 0.53 in the narrowest section of the calibrated orifices.

12. The measurement station according to claim 10, wherein the at least two calibrated orifices define a gas stream at critical regime of less than $1.69 \text{ Pa} \cdot \text{m}^3/\text{s}$.

13. The measurement station according to claim 10, wherein the at least two calibrated orifices have a dimension less than 6/10 mm.

14. The measurement station according to claim 10, wherein a throughput of the conditioning pump is greater than $25.35 \text{ Pa} \cdot \text{m}^3/\text{s}$.

15. The measurement station according to claim 10, wherein the at least two calibrated orifices have a dimension less than 4/10 mm.

* * * * *